(12) United States Patent
McMichael

(10) Patent No.: US 11,166,881 B2
(45) Date of Patent: Nov. 9, 2021

(54) TUBE CLEANING ACTUATED SYRINGE

(71) Applicant: Avent, Inc., Alpharetta, GA (US)

(72) Inventor: Donald McMichael, Roswell, GA (US)

(73) Assignee: Avent, inc., Alpharetta, GA (US)

( * ) Notice: Subject to any disclaimer, the term of this patent is extended or adjusted under 35 U.S.C. 154(b) by 239 days.

(21) Appl. No.: 16/112,989

(22) Filed: Aug. 27, 2018

(65) Prior Publication Data

US 2020/0060941 A1   Feb. 27, 2020

(51) Int. Cl.
*A61J 15/00* (2006.01)
*B08B 9/032* (2006.01)
*B08B 9/035* (2006.01)

(52) U.S. Cl.
CPC ........... *A61J 15/0026* (2013.01); *B08B 9/035* (2013.01); *B08B 9/0321* (2013.01); *B08B 2209/022* (2013.01); *B08B 2209/032* (2013.01)

(58) Field of Classification Search
CPC .... A61J 15/00; A61J 15/0026; A61J 15/0096; B08B 2209/00; B08B 2209/02; B08B 2209/27; B08B 9/032; B08B 9/0326; B08B 2209/022; B08B 2209/032; B08B 9/0321; B08B 9/035; A61M 2005/1403; A61M 2025/0019; A61M 25/00; A61M 5/1452; A61M 5/20
See application file for complete search history.

(56) References Cited

U.S. PATENT DOCUMENTS

| | | | |
|---|---|---|---|
| 4,977,517 A * | 12/1990 | Gibbs, Jr. | G01N 15/12 |
| | | | 128/DIG. 13 |
| 5,876,378 A * | 3/1999 | Mbadugha | A61M 31/005 |
| | | | 604/152 |
| 7,172,572 B2 | 2/2007 | Diamond et al. | |
| 8,262,610 B2 | 9/2012 | Duchon et al. | |
| 8,764,912 B2 | 7/2014 | Kuroda | |
| 9,308,326 B2 | 4/2016 | Hunter et al. | |
| 9,308,348 B2 | 4/2016 | Mulvihill et al. | |
| 9,332,894 B2 | 5/2016 | Cheng et al. | |

(Continued)

FOREIGN PATENT DOCUMENTS

| | | |
|---|---|---|
| EP | 3 222 307 A1 | 9/2017 |
| JP | 2001337094 A | 12/2001 |
| WO | WO 99/52575 A1 | 10/1999 |

OTHER PUBLICATIONS

International Search Report and Written Opinion for PCT/US2019/046987, dated Dec. 5, 2019, 15 pages.

*Primary Examiner* — Jason E Flick
(74) *Attorney, Agent, or Firm* — Dority & Manning, P.A.

(57) ABSTRACT

Devices for cleaning a tube or clearing a blockage from a tube, such as an enteral feeding device are provided. The devices include an actuator and a syringe. The actuator is releasably attached to the syringe in a manner that allows the actuator to transition the syringe from a compressed position to an extended position, and vice-a-versa, without requiring the intervention of a user. A method of cleaning a tube or clearing a blockage in a tube is also provided. The tube cleaning device is filled with a liquid and the actuator pushes the liquid from the syringe into the tube when transitioning into a compressed position, and withdraws the liquid back into the syringe when transition into an extended position, causing the liquid to contact a blockage, and clear the blockage and/or clean the tube.

20 Claims, 4 Drawing Sheets

(56) References Cited

U.S. PATENT DOCUMENTS

| | | | |
|---|---|---|---|
| 9,333,293 B2 | 5/2016 | Williams et al. | |
| 9,357,950 B2 | 6/2016 | Mendels et al. | |
| 2012/0291811 A1* | 11/2012 | Dabney | B08B 9/0321 134/18 |
| 2013/0237930 A1 | 9/2013 | Mulvihill et al. | |
| 2014/0102445 A1 | 4/2014 | Clement et al. | |
| 2016/0317393 A1* | 11/2016 | Davis | A61M 5/345 |

\* cited by examiner

TUBE CLEANING ACTUATED SYRINGE

BACKGROUND

Numerous situations exist in which anatomical structures of the human body need to be catheterized through an artificial stoma to achieve a desired medical goal. Relatively common situations are for drainage of retained fluids and administering nutritional solutions or medicines directly into the stomach or intestines. For these situations a stoma is formed percutaneously and an indwelling device is placed through the stoma. By way of example the surgical opening and/or the procedure to create a stoma spanning between the stomach or intestinal wall and the exterior of the skin is commonly referred to as "gastrostomy." A device with a catheter component, e.g., a feeding tube, placed through such a stoma allows injection of feeding solutions through the tube to provide nutrients directly to the stomach or intestines (known as enteral feeding).

As indicated above, there are a variety of instances in which it may be necessary to use a catheter, one of which is the not uncommon reaction following major surgery in which a patient's stomach function is impaired for a period of time. In addition to the need to supply or supplement the body with a certain level of nutrients and the like following surgery as well as in other instances of impaired or limited gastric functionality, a further issue is that an unfed gut can become a source of bacteria that gets into the bloodstream. These types of problems may be resolved by the introduction of nutrients through an enteral feeding device tube properly inserted through the patient's abdominal wall, gastric wall, pylorus, duodenum, and/or into the jejunum beyond the Ligament of Treitz.

However, the nutrients used are generally in the form of a formula that has a viscous liquid or semi-solid consistency. As such, a problem exists in that the tubing used in catheters, such as an enteral feeding device, tends to become clogged or blocked. Further, many catheters used for feeding are also used to administer medications and supplements to the mammal. Such medications and supplements often have a powdery or chalky consistency and can easily cause blockages or clogs if not fully flushed through the catheter, either exacerbating issues caused by a feeding formula or standing alone.

Currently, when a blockage occurs, a user is typically required to attach a syringe and manually administer a suction-pressure cycle until the blockage is cleared. For instance, the instructions for use ("IFU") generally state, "[p]lace a catheter tip syringe filled with warm water into the appropriate lumen of the tube and gently pull back on then depress the plunger to dislodge the clog. If the clog remains, repeat previous step. Gentle suction alternating with syringe pressure will relieve most obstructions." However, the IFU provides no interpretation of gentle suction and pressure, often times resulting in a user collapsing a tube from too much suction, rupturing the tube from too much pressure, or not applying enough of either suction or pressure, resulting in the clog or blockage failing to be removed.

Further devices have been evolved to clear blockages, but such devices often times require the use of automatic devices such as brush tube cleaners or boring devices. Known automatic devices often need to be inserted into the tubing to a point where the device contacts the blockage, and are not compatible for use in most care situations outside of a hospital.

Therefore, it would be beneficial to provide a tube cleaning device that is easy to use for at home or out of hospital care. It would also be beneficial to provide a tube cleaning device that does not require a device or automatic tool to be inserted into the tubing to a point that contacts the blockage. Further, it would be an advantage to have a tube cleaning device that may automatically sense when an adequate amount of suction and/or pressure has been applied to the tubing. It would also be advantageous to have a tube cleaning device that automatically continues a cleaning cycle until a clog or blockage has been cleared. Further, it would be beneficial to have a tube cleaning device that may be used to clean a catheter, such as a feeding tube, and that may also be capable of clearing a blockage or clog in a catheter.

SUMMARY

Aspects and advantages of the invention will be set forth in part in the following description, or may be obvious from the description, or may be learned through practice of the invention.

The present disclosure is generally directed to a tube cleaning device. The tube cleaning device includes an actuator and a syringe. The actuator is releasably attached to the syringe, and is configured to automatically transition a syringe from an extended position to a compressed position.

In a further embodiment, the actuator is a linear actuator. Additionally or alternatively, the actuator is further configured to transition the syringe from the compressed position to the extended position. Moreover, in one embodiment, the actuator stops the transition of the syringe from the extended position to the compressed position, the compressed position to the extended position, or both the transition from the extended position to the compressed position and the transition from the compressed position to the extended position, at a preset pressure or distance travelled.

In an additional or alternative embodiment, the syringe contains a reservoir, where the reservoir has a size sufficient to contain an amount of a liquid of from about 10 milliliters to about 100 milliliters. In one embodiment, the actuator is battery operated. In yet a further embodiment, the actuator comprises a pressure sensor. Additionally or alternatively, the syringe contains a reservoir that has a tip, where the tip is configured to connect to an enteral feeding device. In a further embodiment, the actuator is releasably attached to the syringe. Additionally or alternatively, the reservoir has a diameter of from about 5 millimeters to about 50 millimeters.

The present disclosure also generally includes a method of cleaning a tube. The method includes filing a reservoir of a tube cleaning device with an amount of liquid, and connecting the tube cleaning device to a tube. The tube cleaning device includes an actuator and a syringe. The actuator is releasably attached to the syringe, and is configured to transition a syringe from an extended position to a compressed position.

In a further embodiment, the tube is an enteral feeding device. In one embodiment, the liquid is pushed through a tip of the reservoir into the tube when the actuator transitions the syringe into the compressed position. Additionally or alternatively, the liquid is withdrawn back into the reservoir from the tube when the actuator transitions the syringe into the extended position. In yet a further embodiment, the actuator stops the transition of the syringe from the extended position to the compressed position, the compressed position to the extended position, or both the transition from the extended position to the compressed position and the transition from the compressed position to the extended position, at a preset pressure or distance travelled.

In an additional or alternative embodiment, the actuator stops the transition of the syringe automatically upon reaching the preset pressure without requiring intervention by a user.

The present disclosure also generally includes a method of removing a blockage from a tube. The method includes filing a reservoir of a tube cleaning device with an amount of liquid, and connecting the tube cleaning device to a tube. The tube cleaning device includes an actuator and a syringe. The actuator is releasably attached to the syringe, and is configured to transition a syringe from an extended position to a compressed position.

In one embodiment, the liquid is pushed through a tip of the reservoir into the tube when the actuator transitions the syringe into the compressed position. Additionally or alternatively, the liquid is withdrawn back into the reservoir from the tube when the actuator transitions the syringe into the extended position.

Further, in an embodiment, the liquid is pushed through the tip of the reservoir in an amount sufficient to contact a blockage of the tube. Moreover, in one embodiment, the actuator cycles the liquid between the blockage and the reservoir by repeating transitions of the syringe from the compressed position to the extended position. In an additional or alternative embodiment, the cycles are continued until the blockage has been cleared.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

DETAILED DESCRIPTION

Figure 1A:
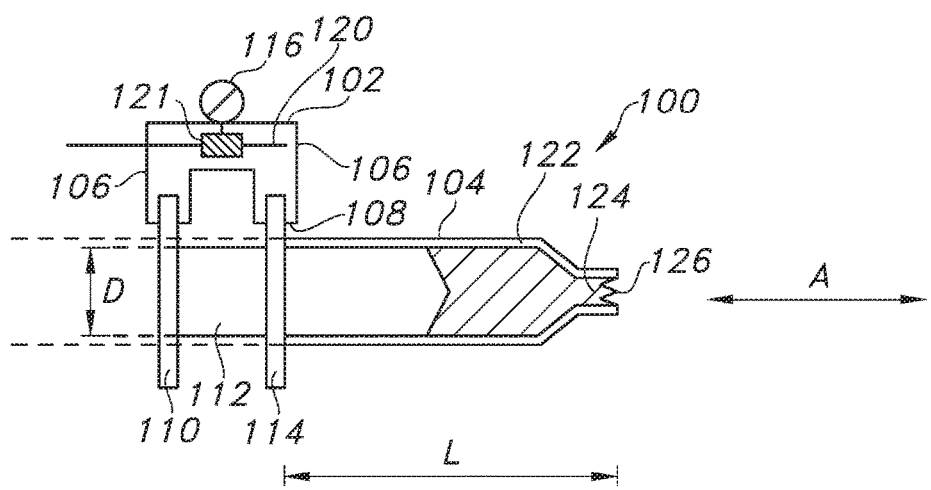
FIG. 1a is a view of a tube cleaning device according to the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Moreover, the particular naming of the components, capitalization of terms, the attributes, data structures, or any other programming or structural aspect is not mandatory or significant, and the mechanisms that implement the invention or its features may have different names, formats, or protocols. Also, the particular division of functionality between the various components described herein is merely exemplary and not mandatory; functions performed by a single component may instead be performed by multiple components, and functions performed by multiple components may instead performed by a single component.

According to the present disclosure, an enteral feeding device may generally refer to an enteral feeding device, such as a feeding tube, that has been inserted into a mammal (e.g. a human).

The present invention relates to a device for cleaning a blockage or a clog in a non-vascular catheter device, e.g., an enteral feeding device or the like including extensions thereof, having a catheter tube, an external retainer (e.g., base deployed outside the human body), and an indwelling retainer that is deployed within a lumen or cavity of a patient's body (i.e., a non-vascular lumen or cavity of the body such as, for example, a gastric lumen, jejunum, peritoneal cavity or the like). For example, the indwelling retainer may be a retention mechanism of the catheter device that prevents the catheter device from being pulled out of the patient, and the indwelling retainer may be inserted into the body lumen through a stoma. The insertion through the stoma may be from outside the body or it may be performed from inside the body using endoscopic techniques. In this context, the term "insertion" should be understood as putting in or introducing the catheter tube in place in a stoma so that the base is deployed outside the human body and the indwelling retainer is deployed within a non-vascular lumen or cavity.

Generally speaking, the present disclosure is directed to a tube cleaning device for clearing clogs or blockages from non-vascular catheters, such as enteral feeding devices utilizing tubing. Particularly, a tube cleaning device according to the present disclosure may utilize an actuator, such as a linear actuator in one embodiment, that is able to compress and extend a pump, such as a syringe, to agitate and remove a blockage or clog. Moreover, the actuator may be at least partially, if not fully automated, such that the actuator is able to agitate the blockage or clog without a user needing to gauge the level of pressure or suction needed. Furthermore, a tube cleaning device according to the present disclosure may be capable of detecting a pressure in a non-vascular catheter, such that the tube cleaning device may select the amount of extension and compression of the pump needed to provide the necessary pressure to clear the clog or blockage without damaging the non-vascular catheter. Of course, while the present disclosure discusses tubing relating to enteral feeding devices, it is also envisioned that the tube cleaning device of the present disclose may be able to effectively clean and clear blockages from other types of tubing known in the art.

Figure 1B:
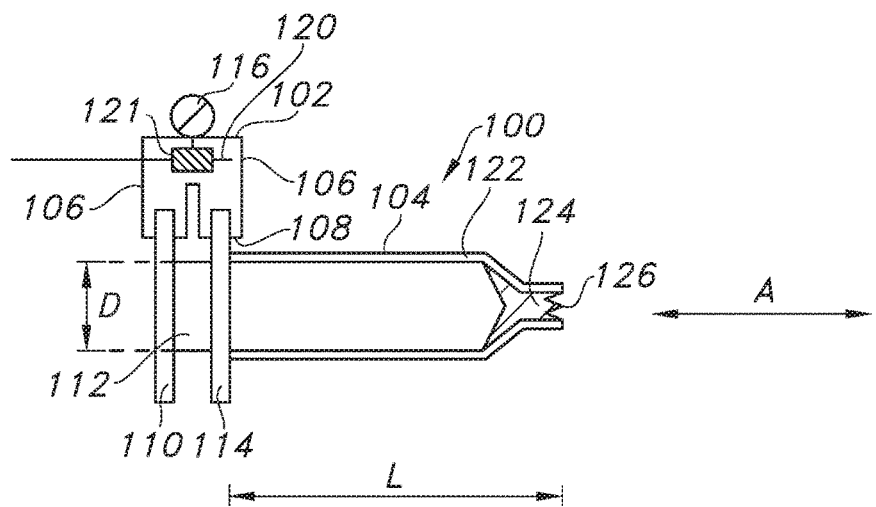
FIG. 1b is a view of the tube cleaning device according to FIG. 1a in compressed position.
Figure 1C:
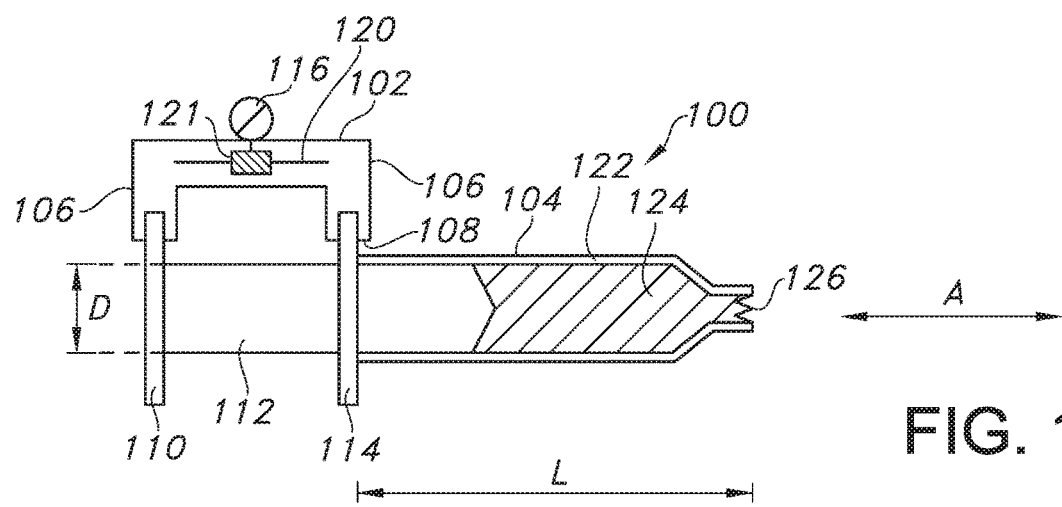
FIG. 1c is a view of the tube cleaning device according to FIG. 1a in an extended position.

For instance, in one embodiment, a tube cleaning device may include an actuator. Referring to FIGS. 1a-1c, a tube cleaning device 100 may include an actuator generally shown by reference character 102. The actuator 102 may be formed integrally with a pump such as a syringe 104, or may be configured to attach to a syringe 104 that is formed separately from the actuator 102. For instance, in one embodiment, the actuator may have arms 106 that contain a seal, pressure sensitive adhesive, or snap fit receiving end, for example, at the distal end 108 of the arms 106. In such a manner, the distal end 108 of the arms 106 of the actuator 102 may be able to releasably attach to the base 110 of the plunger 112 and the lip 114 of the syringe 104. Of course, while not pictured, an actuator 102 according to the present disclosure may attach to the syringe 104 via the arms 106 and/or may have a releasable attachment, such as a pressure sensitive adhesive only on an interior or exterior portion of the arms 106 so as to attach to an interior or exterior portion of the base 110 and the lip 114, instead of encompassing a portion of the base 110 and the lip as shown in FIGS. 1a-1c. Regardless, in one embodiment, the actuator 102 may be attached to the syringe 104, utilized to agitate a blockage or clean a tube, and may then be removed from the syringe 104, using a releasable attachment discussed above or as known in the art.

Nonetheless, regardless of the attachment configuration used, the actuator 102 may have a motor 116. The motor 116 may be operated by any power source as known in the art, but in one embodiment, the motor 116 may be battery operated. Notwithstanding the power source selected, the motor 116 may be attached to the actuator 102 such that the motor 116 may transition the actuator 102 from a compressed position, such as generally shown in FIG. 1b, to an extended position, as generally shown in FIG. 1c, as well as points therebetween, such as generally shown in FIG. 1a, without requiring any action or intervention by a user. Generally, a motor 116 and actuator 102 acting together in the present disclosure may move the actuator arms 106 and the syringe in a substantially linear direction, such as generally shown by the direction of vector A. Thus, in one embodiment, the actuator 102 may be a linear actuator.

The motor 116 may be attached to the actuator 102 and/or segments of the actuator 118 (shown more clearly in FIGS. 2a-2c), in any way known in the art, and in one example, may be connected via a rod 120 on an interior portion of the actuator 102, or alternatively, may be connected via a track on an exterior portion of the actuator 102 (not shown). In one embodiment, the rod 120 is a screw for a ball-screw type mechanism 121. In such an embodiment, the rod 120 may maintain its original length, but the ball-screw type mechanism 121 may cause at least one of the arms 106 of the actuator 102 to move in a linear motion along the rod 120 or vector A.

Figure 2A:
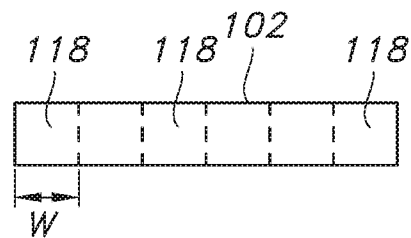
FIG. 2a is a top view of a portion of a tube cleaning device according to the present disclosure.
Figure 2B:
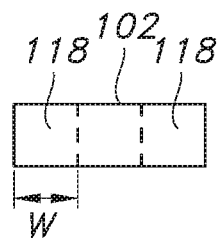
FIG. 2b is a top view of a portion of a tube cleaning device according to FIG. 2a in a compressed position.
Figure 2C:
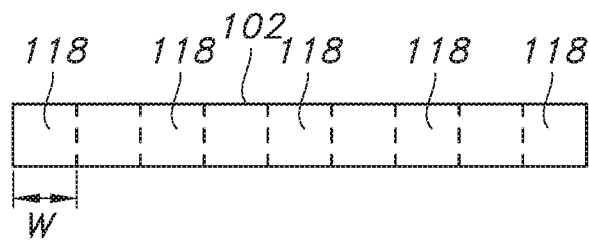
FIG. 2c is a top view of a portion of a tube cleaning device according to FIG. 2a in an extended position.

Referring to FIGS. 2a-2c, in a further embodiment, when the motor 116 is attached to the actuator 102 or individual segments 118 of the actuator 102, the motor 116 may be able to extend the actuator 102 exposing a greater number of the segments 118, such that the actuator is in an extended position, for instance, the position generally shown in FIG. 1c. Similarly, the motor 116 may also be able to contract the actuator 102 or the segments 118 to transition the actuator 102 into a compressed position, such as generally shown in FIG. 1b, where the segments 118 have been compacted to reveal fewer of the segments 118, as generally shown in FIG. 2b. Of course, as discussed above, the motor 116 is also able to transition the actuator 102 into positions between the compressed and extended position, as generally shown in FIGS. 1a and 2a. Thus, in an embodiment, such as an embodiment shown in FIGS. 2a-2c, the rod 120 may be collapsible or deformable, so as to expand and retract along with the segments, or by other attachment to the actuator 102, upon action by the motor 116.

An actuator may be capable of transitioning from an extended to a compressed position, and vice versa, by any means generally known in the art. For instance, in one example, the actuator may be formed of a deformable material, such that the segments 118 are able to deform to a relatively small width, and are then able to be extended back into their extended shape. In such an embodiment, the segments 118 may not be individual pieces or have any delineation from the actuator as a whole, but may be portions of the actuator used to measure an amount of compression. Alternatively, the segments 118 may be individual segments that are able to fold or retract under or within the immediately adjacent segment 118. In such a manner, the segments 118 may not increase or decrease in size moving from one side of the actuator to the other, and instead may work in cooperation with adjacent segments, such that all of the segments could be contained within a single segment. Of course, other manners of compression are contemplated herein as are generally known in the art.

Regardless of the manner of compression used, the actuator may be formed from a material that is capable of compression and extension, and that is capable of applying a force to a plunger of a syringe sufficient to agitate a liquid from a syringe, into a tube, and back into the syringe. In one embodiment, the material may be a high impact plastic, such as an acrylonitrile butadiene styrene, a polycarbonate, a polyetherimide, such as an Ultem® polyetherimide, a co-polyester, such as a Tritan™ co-polyester, or combinations thereof. Of course a hard plastic may be selected that has such a strength, or a weaker material that is more easily deformed may be used and instead may utilize reinforcement in the arms 106 and/or actuator 102 body, such as the collapsible rod 120.

Notwithstanding the material selected or the type of segments used, an actuator according to the present disclosure may be set to deliver a maximum pressure to the tube, where the pressure in the tube is a function of the pressure administered to the liquid contained in the reservoir that is pushed from the reservoir into the tube and the distance of the tubing that the liquid must travel before contacting a blockage or stoppage. For instance, in one embodiment, the actuator may be set to deliver a pressure of between about 4 psi and 10 psi, such as a pressure of between 5 psi to about 9 psi, or in one embodiment, to deliver a pressure of about 7 psi. Thus, a user does not have to guess at a pressure needed to dislodge or break up a clog or blockage, as the actuator is set to expand and compress an amount sufficient to obtain such a pressure. Furthermore, an actuator according to the present disclosure may also have a sensor that is able to detect when a desired pressure has been reached. In such a manner, the sensor may be preset with the desired pressure, and the actuator expands and compresses until that pressure is reached.

Additionally or alternatively, the pressure may not be preset, and instead, the actuator may be present to travel a certain distance, such that the actuator may only extend and compress the plunger of the syringe a distance necessary to obtain the preset distance. However, it should be noted that the two preset values may be used simultaneously. For instance, a preset distance may be used to start the actuator cleaning and/or blockage clearing cycle, however a pressure sensor may stop or restrict the distance if a maximum pressure is reached. In such a way, an actuator may be used based upon a preset distance, pressure, or a combination thereof.

In an embodiment according to the present disclosure, a tube cleaning device according to the present disclosure may also generally include a pump, such as a syringe 104. A syringe 104 according to the present disclosure may be any syringe that is commercially available, and may be formed from such materials as are known in the art. A syringe 104 may have a reservoir 122 that is configured to contain a liquid 124, such as water, as generally shown in FIGS. 1a-1c. Thus, when the actuator 102 transitions into a compressed position, such as generally shown in FIG. 1b, the plunger 112 of the syringe 104 may push or force the liquid 124 out of the reservoir 122 through a tip 126 of the syringe 104; and when the actuator 102 transitions into an extended position, such as generally shown in FIG. 1c, the plunger 112 of the syringe 104 may be drawn away from the tip 126, creating a vacuum in the reservoir 122 and drawing the liquid 124 back into the reservoir 122. While one embodiment of emptying and refilling a reservoir has been described, other methods may be used as generally known in the art.

Thus, in one embodiment, in order to hold an amount of liquid needed to clear a clog or blockage, or clean a tube, the reservoir may have a size such that the reservoir may contain an amount of a liquid of about 10 milliliters to about 100 milliliters, such as an amount of from about 25 milliliters to about 85 milliliters, such as an amount of from about 50 milliliters to about 70 milliliters. Of course, as may be well known in the art, one milliliter is equivalent to one centimeter cubed ($cm^3$). Therefore, the preceding liquid volume measurements may also correspond to an internal volume of the reservoir in cubic centimeters.

In one embodiment, the syringe may thus be a "large bore" syringe. For instance, a reservoir according to the present disclosure may have an inner diameter D of from about 10 millimeters to about 45 millimeters, such as from about 20 millimeters to about 40 millimeters, such as from about 25 millimeters to about 35 millimeters.

Additionally, a reservoir according to the present disclosure may have a length L of from about 35 millimeters to about 400 millimeters, such as from about 50 millimeters to about 300 millimeters, such as from about 75 millimeters to about 200 millimeters, such as from about 85 millimeters to about 175 millimeters. Particularly, by utilizing a syringe having such a length and diameter, a syringe or pump according to the present disclosure may be less unwieldy, allowing a user to more easily attach the syringe to an enteral feeding device, and may also allow for greater surface area and thus, pressure inside the syringe, using less lateral movement by the actuator.

In a further embodiment, the actuator may be used to clean an enteral feeding device or extender thereof, either alternatively, or in addition to removing a blockage. In such an embodiment, an amount of liquid according to the above amounts may be used, however, the actuator may be set to travel a longer distance (e.g. have a longer stroke distance before restarting the extending/compressing cycle by extending and/or compressing the plunger of the syringe a greater distance). Particularly, as noted above, a blockage may serve to build pressure in a tube as it restricts the flow of a liquid. Thus, a tube that is being cleaned and that does not have a blockage may utilize a different pressure or distance setting, as the lack of blockage may affect the pressure measured by the actuator. Thus, an actuator according to the present disclosure may have more than one "mode", such that a travel distance and/or pressure measurement is preset to a different amount when cleaning is needed versus removing a blockage. Additionally or alternatively, in one embodiment, a preset pressure may be used for clearing a blockage and a preset distance may be used for cleaning. However, as discussed above, a preset pressure, a preset distance, or a combination thereof, may be used together for both cleaning and clearing blockages, Regardless, the cleaning function has a further benefit, in that it lessens the burden on the user of creating a proper cycle for a thorough cleaning, which can lengthen the lifespan of the tube, tubing extension, and/or extension set.

Figure 3:
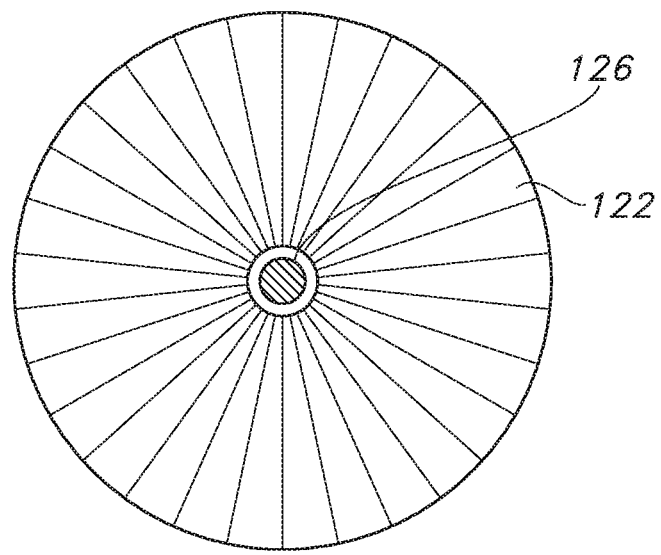
FIG. 3 is a view of a tip of a tube cleaning device for connecting to an enteral feeding device according to the present disclosure.

Nonetheless, referring to FIG. 3, the tip 126 of the reservoir 122 according to the present disclosure may be sized and configured to easily connect to an enteral feeding device or extender thereof. While the tip 126 may have any shape or size that allows passage of the liquid from the reservoir to the enteral feeding device or extender thereof, in one embodiment, the tip 126 may have a shape, material, and/or design that is compatible with an ENFit™ system and/or compatible with systems generally referred to by ISO 80369-3. Thus, in one embodiment, the tip 126 may be designed as an ENFit™ connector. However, as discussed, the tip 126 may also have any dimension necessary to connect to other enteral feeding devices that allows passage of the liquid from the reservoir 126 to the enteral feeding device or extender thereof.

Figure 4A:
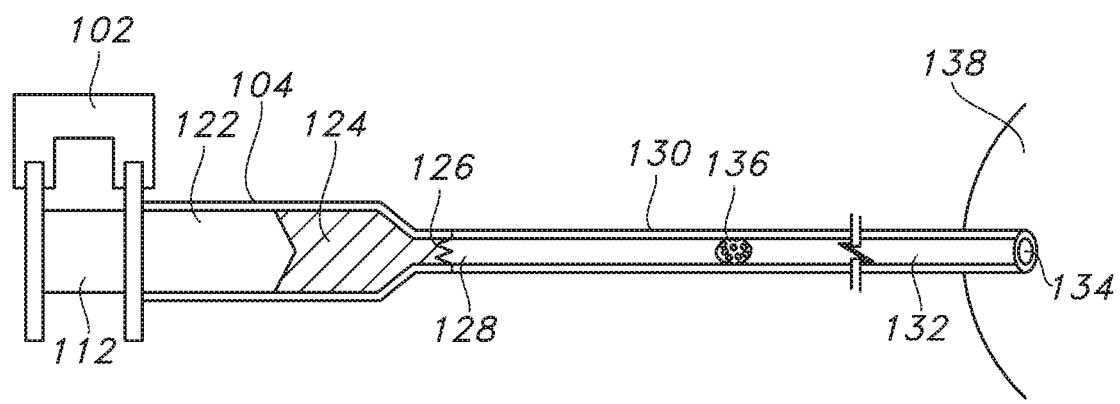
FIG. 4a illustrates clearing a blockage or clog in an enteral feeding device using a tube cleaning device according to the present disclosure.

The present disclosure also generally includes a method of cleaning a tube or breaking up a clog or blockage in a tube using a tube cleaning device as defined herein. For instance, referring to FIGS. 4a to 4c, which may also include further aspects of the tube cleaning device discussed above, a tube cleaning device having an actuator 102 and a syringe 104 has been filled with a liquid 124, such as water. The tip 126 of the syringe 104/reservoir 122 is then connected to a distal end 128 of an enteral feeding device 130, where a distal end 128 of an enteral feeding device 130 is located at an end furthest from the mammal, and wherein the proximal end 132 of the enteral feeding device 130 is adjacent to a side or abdomen of a mammal 138, such that the proximal end 132 may be connected to or may be a port 134.

Figure 4B:
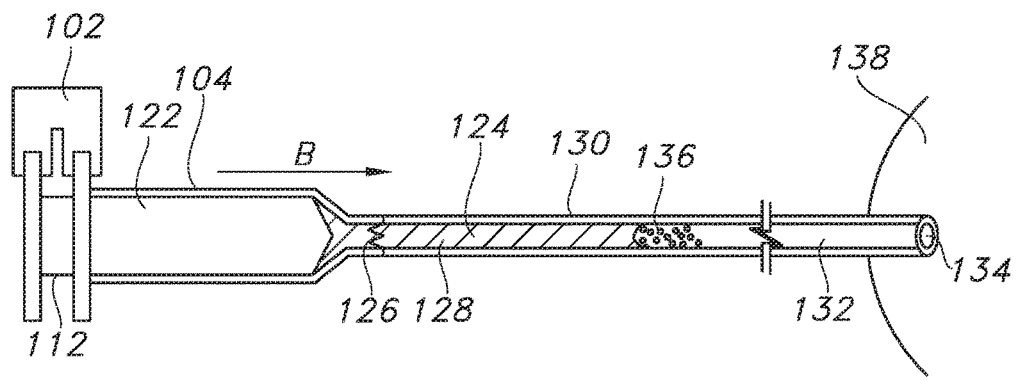
FIG. 4b illustrates clearing a blockage or clog in an enteral feeding device using a tube cleaning device according to the present disclosure.
Figure 4C:
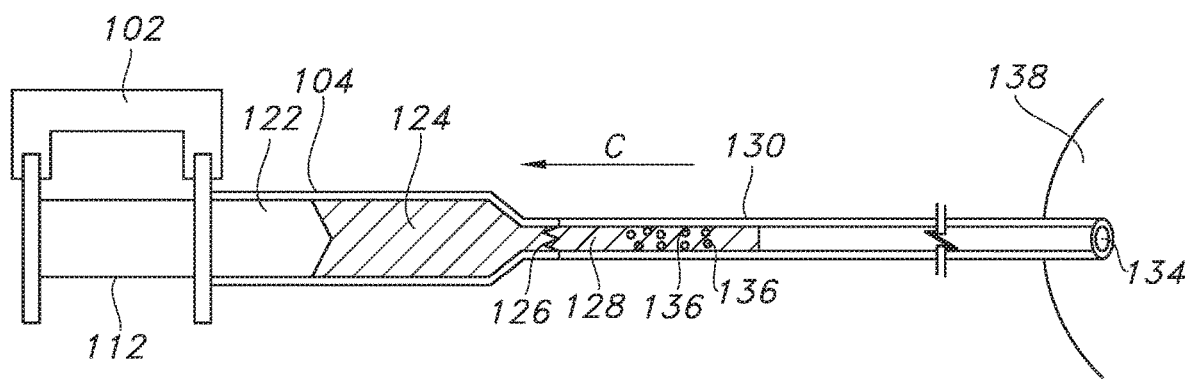
FIG. 4c illustrates clearing a blockage or clog in an enteral feeding device using a tube cleaning device according to the present disclosure.

Regardless, as shown in FIG. 4b, after the syringe 104 has been connected to the enteral feeding device 130, the actuator 102 may transition into a compressed position, transitioning the plunger 112 and syringe 104 into a compressed position, generally along direction B as shown in FIG. 4b. In such a compressed position, the liquid 124 may be pushed from the reservoir 122, through the tip 126, and into the enteral feeding device 130. As discussed above, the actuator 102 may continue to transition to a compressed position until the plunger 112 has moved or travelled a certain distance or a certain pressure in the enteral feeding device tube has been obtained. When the desired pressure or distance has been reached the actuator 102 begins to retract, and transition the plunger 112 and syringe 104 into an extended position, generally along direction C, such as generally shown in FIG. 4c. In transitioning to an extended position, the plunger 112 may create a vacuum in the reservoir 122, causing the liquid 124 to return back into the reservoir 122.

As generally shown in FIG. 4b, the actuator 102 may continue transitioning the syringe 104 and plunger 112 into a compressed position until an amount of liquid 124 has been pushed from the reservoir 122, such that a blockage 136 may be contacted by the liquid 124. Particularly, contacting the blockage 136 with the liquid 124 may cause an increase in pressure necessary to end the transition into the compressed position, as the blockage 136 may fully or partially block the tube, restricting the flow of the liquid. Thus, the actuator 102 may continue to transition the syringe 104 and plunger 112 into a compressed position even after a liquid 124 contacts a blockage or blog 136, until a desired pressure or distance travelled has been reached. After the desired pressure or distance travelled has been reached, the actuator 102 transitions into the extended position, transitioning the syringe 104 and plunger 112 into the extended position, as generally shown in FIG. 4c. In such a position, parts of the blockage 136 may be withdrawn with the liquid 124 during the transition, removing a portion of the blockage. The transition into the extended position may continue until a desired pressure is reached, such as a negative pressure greater than a pressure needed to collapse the tube, but sufficient to withdraw a desired amount of liquid back into the reservoir. The steps may then be repeated, creating a cycle of pressure and suction due to the actuator 102, syringe 104 plunger 112, and the liquid 124, until the blockage has been cleared.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A tube cleaning device comprising:
   an actuator; and
   a syringe, the syringe comprising a tip at a first end, a lip at a second end, and a reservoir extending between the tip and the lip, the syringe further comprising a plunger configured to be inserted in the reservoir, the plunger having a base distal to the second end of the reservoir;
   wherein the actuator is releasably attached to the lip of the syringe and to the base of the plunger, and wherein the actuator is configured to automatically transition a syringe from an extended position to a compressed position;
   wherein the tube cleaning device is configured to connect to a non-vascular catheter; and
   wherein the actuator is configured to agitate a liquid from the syringe into the non-vascular catheter and back into the syringe.

2. The device of claim 1, wherein the actuator is a linear actuator.

3. The device of claim 1, wherein the actuator is further configured to transition the syringe from the compressed position to the extended position.

4. The device of claim 1, wherein the actuator stops the transition of the syringe from the extended position to the compressed position, the compressed position to the extended position, or both the transition from the extended position to the compressed position and the transition from the compressed position to the extended position, at a preset pressure or distance travelled.

5. The device of claim 1, wherein the syringe contains a reservoir, wherein the reservoir has a size sufficient to contain an amount of a liquid of from about 10 milliliters to about 100 milliliters.

6. The device of claim 1, wherein the actuator comprises a pressure sensor.

7. The device of claim 1, wherein the syringe contains a reservoir in fluid communication with the tip, and wherein the tip is configured to connect to an enteral feeding device.

8. The device of claim 7, wherein the reservoir has an interior diameter of from about 5 millimeters to about 50 millimeters.

9. A method of cleaning a non-vascular catheter that has been inserted into a mammal, the method comprising:
   filling a reservoir of a tube cleaning device with an amount of a liquid, the tube cleaning device comprising:
      an actuator; and
      a syringe;
      wherein the actuator is releasably attached to the syringe, and wherein the actuator is configured to transition the syringe from an extended position to a compressed position;
   connecting the tube cleaning device to the non-vascular catheter; and
   agitating the liquid from the syringe into the non-vascular catheter and back into the syringe.

10. The method of claim 9, wherein the non-vascular catheter is an enteral feeding device.

11. The method of claim 9, wherein the liquid is pushed through a tip of the reservoir into the non-vascular catheter, when the actuator transitions the syringe into the compressed position.

12. The method of claim 11, wherein the liquid is withdrawn back into the reservoir from the non-vascular catheter, when the actuator transitions the syringe into the extended position.

13. The method of claim 12, wherein the actuator stops the transition of the syringe from the compressed position, the transition into the extended position, or both the transition into the compressed position and the transition into the extended position, when a preset pressure or distance travelled is reached.

14. The method of claim 13, wherein the actuator stops the transition of the syringe automatically upon reaching the preset pressure or distance without requiring intervention by a user.

15. A method of removing a blockage from a non-vascular catheter that has been inserted into a mammal, the method comprising:
   filling a reservoir of a tube cleaning device with an amount of a liquid, the tube cleaning device comprising:
      an actuator; and
      a syringe;

wherein the actuator is releasably attached to the syringe, and wherein the actuator is configured to transition the syringe from an extended position to a compressed position;

connecting the tube cleaning device to a non-vascular catheter; and agitating the liquid from the syringe into the tube and back into the syringe.

16. The method of claim 15, wherein the liquid is pushed through a tip of the reservoir into the non-vascular catheter, when the actuator transitions the syringe into the compressed position.

17. The method of claim 16, wherein the liquid is withdrawn back into the reservoir from the non-vascular catheter, when the actuator transitions the syringe into the extended position.

18. The method of claim 17, where the liquid is pushed through the tip of the reservoir in an amount sufficient to contact a blockage in the non-vascular catheter.

19. The method of claim 18, where the actuator cycles the liquid between the blockage and the reservoir by repeating transitions of the syringe from the compressed position to the extended position.

20. The method of claim 19, wherein the cycles are continued until the blockage has been cleared.

* * * * *